United States Patent [19]

Reichlin et al.

[11] Patent Number: 5,681,700
[45] Date of Patent: Oct. 28, 1997

[54] ASSAY FOR PATHOGENICITY OF ANTI-DNA ANTIBODIES

[75] Inventors: Morris Reichlin; Eugen Koren, both of Oklahoma City, Okla.

[73] Assignee: Oklahoma Medical Research Foundation, Oklahoma City, Okla.

[21] Appl. No.: 249,387

[22] Filed: May 25, 1994

[51] Int. Cl.$^6$ .................................................. G01N 33/53
[52] U.S. Cl. ......................... 435/6; 435/7.1; 435/7.21; 435/965; 436/518; 436/529
[58] Field of Search ........................... 435/6, 975, 7.1, 435/7.21, 7.92, 965; 436/811, 518, 529

[56] References Cited

FOREIGN PATENT DOCUMENTS

| | | |
|---|---|---|
| 0 276 984 A2 | 8/1988 | European Pat. Off. . |
| 0 295 719 A3 | 12/1988 | European Pat. Off. . |
| 0 307 858 A2 | 3/1989 | European Pat. Off. . |
| 0 313 156 A1 | 4/1989 | European Pat. Off. . |
| 0 438 259 A1 | 7/1991 | European Pat. Off. . |
| 2 682 113 A1 | 4/1993 | European Pat. Off. . |
| WO 90/10229 | 9/1990 | WIPO . |
| WO 95/32430 | 11/1995 | WIPO . |

OTHER PUBLICATIONS

Lundberg et al, British Journal of Rheumatology, 31(12):811–817, 1992.
Baxter Diagnostic Inc. 1991/1992 Catalogue p. 334.
Ravirajan et al, Lupus (England), May 1992, 1(3):157–65.
Terborg et al, J. Rheumatol. 1991, 18(3): 363–367.
Jacob et al, PNAS USA, 1984, 81: 3843–3845.
Raz et al, Eur. J. Immunol., 1993, 23:383–390.
Aarden, L. A., et al., "Immunology of DNA. II. Crithidia luciliae, a Simple Substrate for the Determination of Anti–dsDNA with the Immunofluorescence Technique", Ann. NY Acad. Sci. 254 (1975) 505–515.
Barada, Franc A., et al., "Antibodies to Sm in Patients with Systemic Lupus Erythematosus", Arthritis Rheum., 24 (1981)1236–1244.
Beaulieu, Andre, et al. "IgG Antibodies to Double–Stranded DNA in Systemic Lupus Erythematosus Sera", Arthritis Rheum.,22(1979) 565–570.
Borel, Y., et al, "Oligonucleotide Linked to Human Gammaglobulin Specifically diminishes Anti–DNA Antibody formation in Cultured Lymphoid Cells from Patients with Systemic Lupus Erythematosus", J. Clin. Invest., 82 (1988) 1901–1907.
Borel, Y., et al., "Prevention of Murine Lupus Nephritis by Carrier–Dependent Induction of Immunologic Tolerance to Denatured DNA", Science, 182 (1973) 76–78.
Borel, Y., et al., "Treatment of Lupus Nephritis in Adult (NZB+NZW)F$_1$ Mice by Cortisone—Facilitated Tolerance to Nucleic Acid Antigens", J. Clin, Invest., 61 (1978) 276–286.
Clackson, T., et al. "Making Antibody Fragments using Phage Display Libraries", Nature, 352 (1991) 624–628.
Clark, G. M., et al., "Characterization of a Soluble Cytoplasmic Antigen Reactive with Sera from Patents with Systemic Lupus Erythmatosus", J. Immunol, 102 (1969) 117–122.
Daugherty, B. L., et al., "Polymerase chain reaction facilitates the cloning, CDR–grafting, and rapid expression of a murine moclonal antibody directed against the CD18 component of leukocyte integrins", Nucl. Acids Res., 19 (1991) 2471–2476.
DiValerio, R., et al., "Anti–DNA Antibodies can react specifically with DNA in the context of Glomeruli", Clin. Res., 42 (1994) 139A.
Geysen, H. M., et al., "Use of Peptide Synthesis to probe Viral Antigens for Epitopes to a resolution of a Single Amino Acid", Proc. Nat. Acad. Sci. USA, 81 (1984) 3998–4002.
Hamilton, R. G., et al., "Two Ro(SS–A) Autoantibody responses in Systematic Lupus Erythematosus", Arthritis Rheum., 31 (1988) 496–505.
Harley, J. B., et al., "A Model for Disease Heterogeneity in Systemic Lupus Erythematosus", Arthritis and Rehumatism, 32 (1989) 826–836.
Handwerger, B., et al., "Palmerston North Mice Produce Antibodies to U$_1$RNP and SM Particles", Clin. Res., 42 (1994) 315A.
Kabat, E. A., et al.1, Sequences of Proteins of Immunological Interest, 4th Ed. (U.S. Dept. Health and Human Services, Bethesda, MD, 1987).
Koffler, D., et al., "Antibodies to Polynucleotides in Human Sear: Antigenic Specificity and Relation to Disease", J. Exp. Med., 134 (1971) 294–312.
Maddison, P. J., et al., "Deposition of Antibodies to a Soluble Cytoplasmic Antigen in the Kidneys of Patients with Systemic Lupus Erythematosus", Arthritis Rheum., 22 (1979) 858–863.
Maddison, P. J., et al., "Patterns of Clinical Disease Associated with Antibodies to Nuclear Ribonucleoprotein", J. Rheumatol., 5 (1978) 407–411.
Mattioli, M., et al., "Heterogeneity of RNA Protein Antigens Reactive with Sear of Patients with Systemic Lupus Erythematosus", Arthritis Rheum., 17 (1974) 421–429.
Mattioli, M., et al., "Characterization of a Soluble Nuclear Ribonucleprotein Antigen Reactive with SLE Sera", J. Immunol., 107 (1971) 1281–1290.

(List continued on next page.)

Primary Examiner—Paula K. Hutzell
Assistant Examiner—Patricia A. Duffy
Attorney, Agent, or Firm—Arnold Golden & Gregory

[57] ABSTRACT

Assays that are prognostic for patients that will develop nephritis have been developed where patient serum is screened for the presence of anti-dsDNA antibodies that are cross reactive with A and D SnRNP proteins. The assays are based on the use of either peptides containing epitopes bound by the anti-dsDNA antibodies, or the antigens for the antibodies, A and D SnRNP proteins. Therapeutic compositions have also been developed using either antibodies that block the pathogenicity of the anti-dsDNA antibodies, such as the naturally occurring anti-La/SSB and anti-U$_1$RNP antibodies that are cross reactive with the anti-dsDNA or using the peptides or A and D proteins to induce tolerance.

2 Claims, No Drawings

OTHER PUBLICATIONS

Miniter, M. F., et al., "Reassessment of the Clinical Significance of Native DNA Antibodies in Systemic Lupus Erythematosus", *Arthritis Rheum.*, 22 (1979) 959–968.

Pennebaker, J. B., et al. "Immunoglobulin classes of DNA Binding Activity in Serum and Skin in Systemic Lupus Erythematosus", *J. Clin. Invest.*, 60 (1977) 1331–1338.

Provost, T. T., et al., "Lupus Band Test in Untreated SLE Patients: Correlation of Immunoglobulin Deposition in the Skin of the2 extensor Forearm with Clinical Renal Disease and Serological Abnormalities", *J. Invest. Dermatol.*, 74 (1980) 407–412.

Reichlin, M., et al. "Correlation of a Precipitin Reaction to an RNA Protein Antigen and a Low Prevalence of Nephritis in Patients with Systemic Lupus Erythematosus", *N. Engl. J. Med.*, 286 (1972) 908–911.

Reichlin, M., "Measurement of Antibodies to Sm and nRNP by Eliza: Clinical and Serological Correlations", *Mixed Connective Tissue Disease and Anti-Nuclear Antibodies: Proceedings of the International Symposium on Mixed Connective Tissue Disease and Anti-nuclear Antibodies, Tokyo*, (29–30 Aug. 1986) 85–87.

Reichlin, M., et al. "Lupus Autoantibodies to Native DNA Cross–React with the A and D SnRNP Polypeptides", *J. Clin. Invest.*, 93 (1994) 443–449.

Schur, P.H. and Sandson, J. N., "Immunologic Factors and Clinical Activity in Systemic Lupus Erythematosus", *Engl. J. Med.*, 278 (1982) 533–538.

Sharp, G. C., et al., "Mixed Connective Tissue Disease—An Apparently Distinct Rheumatic Disease Syndrome Associated with a Specific Antibody to an Extractable Nuclear Antigen (ENA)", *The American Journal of Medicine*, 52 (1972) 148–159.

Talal, N., et al., "Immunologic regulation of spontaneous antibodies to DNA and RNA. I. Significance of IgM and IgG Antibodies in SLE Patients and Asymptomatic Relatives", *Clin. Exp. Immunol.*, 25 (1976) 377–382.

Tan, E. M., et al., "Deoxyribonucleic Acid (DNA) and Antibodies to DNA in the Serum of Patients with Systemic Lupus Erythematosus", *J. Clin Invest.*, 45 (1966) 1732–1740.

Tan, E. M., et al., "Characteristics of a Soluble Nuclear Antigen Precipitating with SEAR of Patients with Systemic Lupus Erythematosus", *J. Immunol.*, 99 (1966) 464–471.

Tsao, B. P., et al., "Structural Characteristics of the Variable Regions of Immunoglobulin Genes Encoding a Pathogenic Autoantibody in Murine Lupus", *J. Clin. Invest.*, 85 (1990) 530–540.

Vlahakos, D., et al., "Murine Monoclonal Anti–DNA Antibodies Penetrate Cells, Bind to Nuclei and Induce Glomerular Proliferation and Proteinuria In Vivo", *J. Am. Soc. Nephrol.* 2 (1992) 1345–1354.

Wasicek, C. A., et al., "Clinical and Serological Differences between Systemic Lupus Erythematosus Patients with Antibodies to Ro Versus Patients with Antibodies to Ro and La", *J. Clin Invest.*, 69 (1982) 835–843.

Winfield, J. B., et al., "Specific Concentration of Polynucleotide Immune Complexes in the Cryoprecipitates of Patients with Systemic Lupus Erythematosus", *J. Clin. Invest.*, 56 (1975) 563–570.

Winkler, T. H., et al., "IgG Human Monoclonal Anti–DNA Autoantibodies from Patients with Systemic Lupus Erythematosus", *Clin. Exp. Immunol.*, 85 (1991) 379–385.

ASSAY FOR PATHOGENICITY OF ANTI-DNA ANTIBODIES

BACKGROUND OF THE INVENTION

The present invention includes methods and reagents for assessment of pathogenicity of antibodies to double stranded (ds) DNA and development of specific therapy based on anti-idiotypes to anti-dsDNA.

BACKGROUND

Relationship of antibodies to dsDNA, the RNAproteins Ro/SSA, La/SSB, $U_1$RNP, and Sm, and clinical disease expression.

The laboratory directed by Morris Reichlin at the Oklahoma Medical Research Foundation, Oklahoma City, Okla., has been engaged in the study of autoimmune responses to RNAprotein antigens in SLE patients for over 20 years. Researchers have reported the initial descriptions of the Ro/SSA (Clark, G. M., Reichlin, M. and Tomasi, T. B. *J. Immunol.*, 102:117–122 (1969)), La/SSB (Mattioli, M. and Reichlin, M. *Arthritis Rheum.*, 17:421–429 (1974)), and nRNP($U_1$RNP) (Mattioli, M. and Reichlin, M. *J. Immunol.*, 107:1281–1290 (1971)) systems, while others described the Sm antigen (Tan, E. M. and Kunkel, H. G. *J. Immunol.*, 99:464–471 (1966)).

Over time, it has become apparent that certain profiles of anti-RNAprotein antibodies are positively correlated with nephritis while other profiles are "negatively" correlated or "protected" from the development of serious renal disease. Thus, antibodies to nRNP($U_1$RNP) alone were found to have a low frequency of nephritis (Sharp, G. C., et al. *Am. J. Med.*, 52:148–159 (1972); Reichlin, M. and Mattioli, M. *N. Engl. J. Med.*, 286:908–911 (1972)) while patients with both anti-nRNP and anti-Sm (or anti-Sm alone) had a high frequency of nephritis (Reichlin, M. and Mattioli, M. *N. Engl. J. Med.*, 286:908–911 (1972); Maddison, P. J., et al. *J. Rheumatol.*, 5:407–411 (1978)). In patients with anti-Ro/SSA alone, a high frequency of nephritis was noted (Wasicek, C. A. and Reichlin, M. *J. Clin. Invest.*, 69:835–843 (1982); Hamilton, R. G., et al., *Arthritis Rheum.*, 31:496–505 (1988); Harley, J. B., et al. *Arthritis Rheum.*, 32(7):826–836 (1989)), while in those with both anti-Ro/SSA and anti-La/SSB, a low prevalence of nephritis was found. Studies of acid eluates from lupus nephritis kidneys have demonstrated enrichment of anti-Ro/SSA compared to serum levels (Maddison, P. J. and Reichlin, M. *Arthritis Rheum.*, 22:858–863 (1979)), supporting the participation of Ro/SSA-anti-Ro/SSA complexes in the development and/or the perpetuation of the nephritis. Elution studies of antibodies to the $U_1$RNP/Sm complex also showed enrichment, but the precise specificities of these complexes (anti-Sm or anti-nRNP) were not determined because of technical limitations (Koffler, et al. *J. Exp. Med.*, 134:294–312 (1971)). Serum levels of anti-Sm antibodies have been shown to fluctuate with disease activity (including nephritis) in some SLE patients (Barada, et al., *Arthritis Rheum.*, 24:1236–1244 (1981)). These data indicate a role for the Ro/SSA and Sm systems in the development of nephritis, but only 50% of patients with either anti-Ro/SSA alone or anti-nRNP and anti-Sm (or anti-Sm alone) develop nephritis.

Much data support a major role for the DNA-anti-DNA anti-DNA system in the pathogenesis of lupus nephritis. Clinical studies show that high serum anti-DNA levels correlate positively with the activity of nephritis, and that remissions are associated with declining anti-DNA levels (Harley, et al., *Arthritis Rheum.* (1989); Tan, et al. *J. Clin Invest.*, 45:1732–1740 (1966); Schur, P. H. and Sandson, J. *N. Engl. J. Med.*, 278:533–538 (1982)). Anti-DNA has been shown to be enriched in serum cryoglobulins (Winfield, et al., *J. Clin. Invest.*, 56:563–570 (1975)) and in acid eluates of lupus nephritis kidneys (Maddison and Reichlin (1979); Miniter, et al., *Arthritis Rheum.*, 22:959–968 (1979); Beaulieu, et al. *Arthritis Rheum.*, 22:565–570 (1979)). In all these studies, the specificity of these antibodies are to dsDNA (double stranded or native DNA).

Studies have been reported in the literature describing differences in the ability of murine monoclonal antibodies to dsDNA to induce nephritis when hybridomas producing these antibodies are placed in normal mice (Tsao, et al. *J. Clin. Invest.*, 85:530–540 (1990)). Others have shown that murine monoclonal antibodies penetrate cells, bind to nuclei, and induce glomerular proliferation and proteinuria in vivo (Vlahakos, et al., *J. Am. Soc. Nephrol.* 2:1345–1354 (1992)). Most recently, others have reported direct in vitro binding of murine monoclonal antibodies to glomeruli which is DNA dependent (DiValerio, et al., *Clin. Res.*, 42:139A (1994)).

However, many questions remain about the mechanisms of lupus nephritis and especially the correlations that can be drawn from samples of the most accessible body fluid, the plasma. First, as many as 30% of lupus nephritis patients have never had measurable antibodies to dsDNA in their plasma. Second, as many as 25% of lupus patients with anti-dsDNA in their plasma do not develop nephritis even after many years. It is conceivable that in the first group of patients that anti-dsDNA is never detected in the plasma, because it is immediately complexed with antigen and deposited in the kidney and elsewhere. No one has studied the kidneys of such patients to see if there are large renal deposits composed of DNA and anti-DNA. Some anti-DNA populations may not be nephritogenic because: (1) of poor complement fixing capacity (Miniter, et al., (1979) or Beaulieu (1979)), or (2) because they are largely IgM in nature (Pennebaker, et al. *J. Clin. Invest.*, 60:1331–1338 (1977); Provost, et al., *J. Invest. Dermatol.*, 74:407–412 (1980); Talal, et al., *Clin. Exp. Immunol.*, 25:377–382 (1976)). These two latter observations may not be mutually exclusive, but systematic studies to assess their independent contributions when both are present have not been done. Other molecular factors that have been correlated with "pathogenicity" include high avidity, IgG isotype, high cationic charge, ability to precipitate with DNA, direct binding to glomeruli in vitro, and ability to bind DNA planted in glomerular structures. Thus, the presence of anti-DNA does not always lead to nephritis nor does its consistent absence in the plasma assure protection from serious nephritis. It may well be that lupus nephritis can develop in the absence of antibodies to dsDNA. What is clearly lacking in available diagnostic armamentarium is the ability to distinguish "pathogenic" from non-pathogenic antibodies. There are no simple "tests" at present that can distinguish "bad" from "good" or "harmless" anti-dsDNA antibodies.

It is therefore an object of the present invention to provide methods and reagents for assessment of pathogenicity of antibodies to double stranded (ds) DNA.

It is another object of the present invention to develop specific therapy based on anti-idiotypes to anti-dsDNA.

Summary of the Invention

Based on the interpretation of observations regarding a correlation in lupus patient sera between the presence of certain autoantibodies and the lack of, or presence of, nephritis and severity of pathology, assays and treatments have been developed. The initial observations are that the cross reaction of anti-dsDNA antibodies with denatured A and D SnRNP proteins as they exist in Western blot is a marker for pathogenicity of anti-dsDNA in culture. It also supports the hypothesis that the A and D SnRNP protein may be the original immunogenic stimulus leading to the production of anti-dsDNA. These anti-dsDNA antibodies cross reactive with A and D proteins are also unusual in that they are able to penetrate living cells, leading to cell injury and death, which forms further support for the antibodies in patients being responsible for cell death and injury, especially nephritis. The second set of observations is that the presence of certain other autoantibodies, anti-La/SSB or anti-$U_1$RNP, that are cross reactive with the anti-dsDNA antibodies, protect against cell damage and death. Accordingly, patients characterized by the presence of either anti-La/SSB or anti-$U_1$RNP that is cross reactive with the anti-dsDNA do not get as sick and rarely develop kidney disease.

Using these observations, assays that are prognostic for patients that will develop nephritis have been developed where patient serum is screened, preferably by Western blot, for the presence of anti-dsDNA antibodies that are cross reactive with A and D SnRNP proteins. Other immunoassays are also described. The assays are based on the use of either peptides containing epitopes (defined as four to seven amino acids forming a structure bound by the variable region of an antibody) or the whole A and D SnRNP proteins bound by the anti-dsDNA antibodies.

Therapeutic compositions have also been developed using either antibodies that block the pathogenicity of the anti-dsDNA antibodies, such as the naturally occurring anti-La/SSB and the anti-$U_1$RNP antibodies that are cross reactive with the anti-dsDNA or using the antigenic peptides or the whole A and D proteins to induce tolerance.

DETAILED DESCRIPTION OF THE INVENTION

Work is presented which defines a new molecular correlate of anti-dsDNA with a newly discovered cross reaction to two proteins identified as the A and D SnRNP proteins. A prognostic assay based on this cross reaction correlates closely with the pathogenic potential of anti-dsDNA to injure many cell types in tissue culture and also correlates clinically with organ damage; i.e., nephritis. Populations of autoantibodies to the transcription termination factor La/SSB and the splicing factor $U_1$RNP act as antibodies to anti-dsDNA through the idiotype network. These anti-idiotypes can be used to down regulate anti-dsDNA immunologically specific therapy in patients who have active SLE associated with anti-dsDNA.

The data in the examples implicate a previously unrecognized cross reaction of anti-dsDNA with the denatured A and D SnRNP proteins as they exist in Western blot as a marker for pathogenicity of anti-dsDNA for cells in culture. Experiments on cells in tissue culture demonstrate in vitro effects of antibodies to dsDNA which may reflect their in vivo pathogenicity. Since the results of Example 1 were published in Jan. 1994, several additional discoveries not only expand the original findings, but also provide direction for the development of an approach to define the pathogenic potential of anti-dsDNA, as well as a specific method for turning off the anti-dsDNA response; in effect a directed form of immunotherapy that should be much more specific and safer than current methods of immunosuppression. Description of Biochemistry and Immunochemistry of $U_1$RNP and Sm Particles Understanding of the immune responses to the $U_1$RNP and Sm particles has increased as the biochemistry of these particles has been elucidated. The U (uridine rich) particles are composed of a single RNA complexed noncovalently with five common and between one and three unique polypeptides. Antibodies to $U_1$RNP are directed to the unique polypeptides designated 68 kDa (or 70 kDA), A (34 kDa) and C (19 kDa). There are five other common proteins ranging in size from 28 to 12 kDa. Antibodies to Sm are directed to three of the common polypeptides designated B (28 kDa), B' (26 kDa) and D (16 kDa). Thus, anti-nRNP or anti-$U_1$RNP is largely directed to the $U_1$ specific polypeptides of 68 (70), 34 (A) and 19 (C) kDa while anti-Sm is directed to a doublet of 28 and 26 kDa (BB' ) which are closely related, and D, which are found in all the U particles and define the anti-Sm specificity.

Thus, the A protein is a key target for the anti-$U_1$RNP specificity and the D protein a major target for the anti-Sm specificity. The shared antigenicity of the A and D SnRNP proteins was reported by Reichlin, et al., *J. Clin. Invest.*, 93:443–449 (January 1994)).

As has been reported, immune responses to $U_1$RNP alone are associated with a low prevalence of nephritis while a response directed to Sm alone or in combination with $U_1$RNP is associated with a high risk of nephritis (Sharp, et al., (1972); Reichlin and Mattioli (1972); Maddison, et al., (1978)). In the data in the following examples, antibodies to A and D, whether IgG or IgM, are shown to be closely linked with anti-dsDNA. These apparently antigenically unique and structurally non-homologous A and D proteins share an epitope(s) which is the basis for the cross reaction with antibodies to dsDNA. Neither of these phenomena has been previously reported.

These findings lead to an alternate picture of antibodies to dsDNA from several points of view. The presence of this cross reaction of the denatured A and D proteins with anti-dsDNA provides multiple reinforcing stimuli to promote the production of both anti-dsDNA and anti-SnRNP antibodies. They raise the possibility that the A and D proteins might be the original immunogenic stimulus that leads to the production of anti-dsDNA. Finally, the anti-dsDNA antibodies that cross react with the A and D proteins penetrate living cells in culture leading to their injury. This may have relevance to their role in in vivo pathogenesis and can serve as a marker for pathogenic antibodies to dsDNA. Assays for Diagnosis and Prognosis and Reagents As described in Examples 1, 5, 6 and 8, the presence in a patient serum of anti-dsDNA which is immunoreactive with A and D SnRNP is predictive of severity of disease and probability of developing nephritis, if the patient does not also have anti-La/SSB and/or anti-$U_1$RNP which is immunoreactive with the anti-dsDNA.

Peptide-based assay for anti-dsDNA

An immunoassay utilizing a peptide cross-reactive with anti-dsDNA is both diagnostic and provides information about pathogenicity. Identification of peptides is described below in Example 8. Isolation of A and D proteins to which the anti-dsDNA binds is described below. The key feature is that the peptides are immunoreactive with the anti-dsDNA that binds both the A and D SnRNP proteins. The peptides can be made synthetically using standard peptide synthesis, by isolation and enzymatic cleavage of naturally occurring protein and routine screening of fragments by binding to a column having anti-dsDNA antibody coupled thereto, or by expression of all or a part of the gene encoding the A or D SnRNP encoding an epitope present in both proteins bound by the anti-dsDNA.

The immunoassay can be performed in the same way as described in the examples, using Western blots, or immunoprecipitation of patient sera with native or recombinant proteins A and D, in cell extracts or purified form. A number of immunoassays are known to those skilled in the art, where the variables are only whether antigen or antibody is added in the sample or is immobilized to an inert substrate, labeled or detected using an enzyme-substrate or chromagen detection means.

Cell-based assay for anti-dsDNA

An assay using patient sera can also be examined using cell culture studies to screen for autoantibodies which penetrate cell nuclei, as described, for example, in Example 5.

Assay for pathogenicity and nephritis

As described above for detection of anti-dsDNA, one can also screen for the presence of anti-La/SSB antibodies or anti-$U_1$RNP that cross react with the anti-dsDNA, which would be predictive of less severe disease and a lower probability of developing nephritis. Screening initially for the anti-La/SSB or anti-$U_1$RNP is done using either purified La/SSB or $U_1$RNP, prepared as described below.

1. Affinity Isolation of $U_1$RNP and La/SSB.

These methods are based on selection of appropriate human sera, isolation of IgG from these sera, coupling to cyanogen bromide activated Sepharose™, application of tissue extracts (calf thymus and/or human tissue culture cells; e.g., HeLa or Molt-4) and elution of antigenically active materials with 3.5M $MgCl_2$.

For the preparation of anti-$U_1$RNP columns a plasma is selected which gives a single precipitin line with calf thymus extract, immunoprecipitates only $U_1$RNP, and does not react with purified Sm antigen in ELISA. IgG is isolated by passing plasma equilibrated at 0.02M NaCl, pH 7.2, Tris buffered saline (TBS), over a DE52 (Whatman) column equilibrated with the same buffer. IgG passes directly through this column and is only IgG when examined by immunoelectrophoresis. IgG is coupled to Sepharose™ via cyanogen bromide activation according to the manufacturer's instructions. One hundred grams calf thymus tissue is homogenized in a Waring Blender with 3 volumes cold TBS at 4° C. The extract is centrifuged at 18,000 rpm in a Sorval centrifuge for 60 minutes and salt added to the supernatant to a final concentration of 0.5M NaCl. This extract is then passed over the IgG Sepharose™-anti-$U_1$RNP column and washed with TBS adjusted to 0.5M NaCl until the O.D. is less than 0.05 at 280 nM. Protein is eluted with 3.5M $MgCl_2$. The $U_1$RNP is concentrated to a protein concentration of 5.0 mg/ml (Bio-Rad), dialyzed against TBS, and stored at 70° C. This material is active $U_1$RNP by precipitation in agar gel diffusion and for coating plates for quantitative ELISA. It contains all the recognized $U_1$RNP peptides in Western blot: 70 kD, A, BB', C and D.

La/SSB is similarly prepared from calf thymus extract but IgG is prepared from a serum with an anti-La/SSB precipitin. Since all anti-La/SSB sera contain anti-Ro/SSA, extracts are first passed over an IgG anti-Ro/SSA column to remove Ro/SSA antigen. Other operations are the same as for the preparation of $U_1$RNP. La/SSB prepared in this way can be shown to be free of Ro/SSA, $U_1$RNP or Sm by Western immunoblotting.

2. preparation of A and D Proteins from Human $U_1$RNP Prepared from HeLa Cells.

Purification of $U_1$RNP: Hela cells ($2\times10^8$) are collected by centrifugation, washed with 0.02M TBS, sonicated in 10 ml of 0.05M Tris, 0.3M NaCl, 0.05% NP-40, 0.001M $MgCl_2$ at 0° C. for 3 periods of 20 s, and centrifuged at 10,000 g for 60 min at 4° C. The supernatant is passed through the anti-$U_1$RNP affinity column. The column is washed with 0.02M TBS and $U_1$RNP is eluted with 3.5M $MgCl_2$. The eluate is then dialyzed against 0.02M TBS and stored at −70° C.

SDS PAGE and elution of A and D: The purified $U_1$RNP is separated into polypeptides by SDS-PAGE using 3 mm×180 mm×200 mm 12% gel. Strips from both sides of the gel are then cut and stained by 0.32% Coomassie blue R-250 (Bio-Rad). The remainder of the gel is stored at −70° C. The section of the gel containing the A and D polypeptide is identified according to the stained gel strips and isolated. The A and D polypeptides are electroeluted from each section of the gel using the Electroeluter™ (Bio-Rad, Model 422) concentrated by Centricon-10™ (Amicon Division, W.R. Grace & Co.), and stored at −70° C. Recombinant A and D proteins are prepared by standard methods once the appropriate cDNAs are inserted into appropriate expression vectors.

Therapeutic Applicants and Pharmaceutical Compositions

Based on the results in Examples 1 to 6, one can prepare anti-Id reagents (for anti-dsDNA) that can be used to down-regulate the production of anti-dsDNA described in Example 7.

In one embodiment, the free peptide or a conjugate of this peptide can be used in tolerance induction which could ablate anti-dsDNA.

In a second embodiment, reagents that are antibodies to anti-dsDNA (i.e., anti-La/SSB or anti-$U_1$RNP) could be used to down regulate anti-dsDNA production of SLE patients.

Peptide or Protein-based Compositions.

Attempts to influence anti-DNA production in mouse lupus in vivo or in human lymphocytes in vitro, are described by Borel, et al., *Science*, 182:76–77 (1973); Borel, et al., *J. Clin. Invest.*, 61:276–286 (1978); Borel, Y. and Borel, H., *J. Clin. Invest.*, 82:1901–1907 (1988). As described by Borel, et al., oligonucleotides or nucleosides are attached to isologous (same species) IgG and this is allegedly effective in (1) inhibiting the development of an immune response to DNA in murine lupus and decreasing disease severity, and (2) inhibiting human cells from producing anti-DNA in vitro. The "DNA" used here is single stranded or denatured which is not optimal since the most important response in SLE is to native or double stranded DNA. Borel's work provides an appropriate "carrier" for the toleragen, isologous gamma globulin.

As described herein, peptide(s) that are immunoreactive with dsDNA and are derived from the A and D proteins can be used to induce tolerance in a patient. Antibodies to dsDNA are the disease specific pathogenic autoantibodies of the greatest interest. There are two major possibilities: (1) inject free peptide, or (2) inject peptide-coupled to human IgG, for example, coupled using glutaraldehyde or carbodiimide. These two approaches should both induce T cell tolerance. They may also be effective in inducing B cell tolerance. Both approaches are attractive since there is little chance of "boosting" the anti-dsDNA response. Should the latter occur, it can be treated by standard immunosuppressive drugs, alone or in combination with anti-La/SSB or anti-$U_1$RNP, as described below.

Behavior of the peptide or peptide conjugate is first studied in an appropriate animal model in order to determine efficacy and optimal dosages. There are several that could be used, but the most attractive is the Palmerston North Mouse.

It has been shown that these mice, which all produce anti-dsDNA and develop nephritis, also develop anti-$U_1$RNP and Sm responses in almost all the animals with a dominant immune response against the A protein of $U_1$RNP measured in Western blot, as reported by Handwerger, et al., *Clin. Res.* 42:315A (1994). These mice have no detectable antibodies in the first three months of life but rapidly develop them after six months of age and experience a fulminant glomerulonephritis associated with anti-dsDNA antibodies. Dosage would range from 3 to 300 micrograms per mouse given weekly in the first experiments.

The same result obtained by administering peptide or a peptide conjugate can be achieved by coupling recombinant A or D protein to human IgG.

Anti-La/SSB and Anti-$U_1$RNP Antibodies That Are Cross Reactive With Anti-dsDNA Antibodies.

The reactivity of isolated anti-La/SSB and anti-$U_1$RNP with anti-dsDNA from various patients as well as the antibodies unmasked by absorption with La/SSB and $U_1$RNP from individual patients with anti-A and D reactivity, and the public or private nature of these reactivities, can be determined using standard methodology, as described in more detail in Examples 6–8.

Issues in this regard include the pattern of reactivity of anti-La/SSB or anti-$U_1$RNP isolated from an individual patient. In addition to the unmasked anti-A and D from the same patient, specific affinity purified antibodies including (1) unmasked anti-A and D from the same patient, (2) unmasked anti-A and D antibodies from other patients' sera absorbed with La/SSB, (3) unmasked anti-A and D antibodies from other patients' sera absorbed with $U_1$RNP, and (4) affinity purified anti-dsDNA antibodies which cross react with the SnRNP A and D proteins in Western blot, can be used to characterize the anti-La/SSB, anti-$U_1$RNP, and anti-dsDNA antibodies.

The isolated anti-La/SSB (or anti-$U_1$RNP) is pepsin digested, then used to coat Immulon™ plates. The isolated affinity purified unmasked antibodies and anti-dsDNA antibodies, all of which are IgG, can then be assayed for their reactivity with the anti-La/SSB $Fab_2$. Binding is assessed by reactivity with a conjugate of goat anti-human gamma chain specific alkaline phosphatase conjugate. Color is developed with the addition of the substrate para-nitrophenyl phosphate at 405 nm on a Multitek™ scanner.

Specificity is assured by the ability of free La/SSB antigen to block the reactivity of anti-La/SSB with unmasked anti-A and D or anti-dsDNA. Similarly, $U_1$RNP should block the reactivity of anti-$U_1$RNP with unmasked anti-A and D or anti-dsDNA.

Experiments such as these are used to define the sharing or cross reactivity on the one hand, or the individual specificity of these antibodies on the other, in these idiotype network relationships.

Patients having broadly cross reactive antibodies can be plasmapheresed and used as donors for immunotherapy for patients whose anti-dsDNA is reactive with the donor's anti-La/SSB or anti-$U_1$RNP. This then becomes as simple as intravenous plasma therapy.

An alternative approach is to screen recombinant libraries of Ig variable ("V") regions made from cDNA's reverse transcribed from mRNA extracted from peripheral blood lymphocytes from patients who produce anti-La/SSB and/or anti-$U_1$RNP. A number of such libraries can be constructed and then screened for clones reactive with Fab anti-dsDNA but not normal Fab. These can then be used to produce any desired amount of anti-idiotype to anti-dsDNA. Alternatively, murine recombinant monoclonal anti-idiotypic antibodies directed against relevant idiotope(s) on anti-dsDNA can be produced.

This can be accomplished by the use of Pharmacia's (Pharmacia LKB Biotechnology, Sweden) "Recombinant Phage Antibody System" (RPAS), which generates a single-chain Fv fragment (ScFv) that incorporates the complete antigen-binding domain of the antibody. In the RPAS, antibody variable heavy and light chain genes are separately amplified from the hybridoma mRNA and cloned into an expression vector. The heavy and light chain domains are co-expressed on the same polypeptide chain after joining with a short linker DNA which codes for a flexible peptide. This assembly generates a single-chain Fv fragment (ScFv) which incorporates the complete antigen-binding domain of the antibody. Compared to the intact monoclonal antibody, the recombinant ScFv includes a considerably lower number of epitopes, and thereby presents a much weaker immunogenic stimulus when injected into humans. The murine ScFv molecules can be "humanized" to further reduce the immunogenic stimulus presented.

Methods for "humanizing" antibodies, or generating less immunogenic fragments of non-human antibodies, are well known. A humanized antibody is one in which only the antigen-recognized sites, or complementarily-determining hypervariable regions (CDRs) are of non-human origin, whereas all framework regions (FR) of variable domains are products of human genes.

These "humanized" antibodies present a lesser xenograft rejection stimulus when introduced to a human recipient.

To accomplish humanization of a selected mouse monoclonal antibody, the CDR grafting method described by Daugherty, et al., *Nucl. Acids Res.*, 19:2471–2476, 1991, incorporated herein by reference, can be used. Briefly, the variable region DNA of a selected animal recombinant anti-idiotypic ScFv is sequenced by the method of Clackson, T., et al., *Nature*, 352:624–688, 1991, incorporated herein by reference. Using this sequence, animal CDRs are distinguished from animal framework regions (FR) based on locations of the CDRs in known sequences of animal variable genes. Kabat, H. A., et al.1, Sequences of Proteins of *Immunological Interest*, 4th Ed. (U.S. Dept. health and Human Services, Bethesda, Md. 1987). Once the animal CDRs and FR are identified, the CDRs are grafted onto human heavy chain variable region framework by the use of synthetic oligonucleotides and polymerase chain reaction (PCR) recombination. Codons for the animal heavy chain CRDs, as well as the available human heavy chain variable region framework, are built in four (each 100 bases long) oligonucleotides. Using PCR, a grafted DNA sequence of 400 bases is formed that encodes for the recombinant animal CDR/human heavy chain FR protection.

The present invention will be further understood by reference to the following examples.

EXAMPLE 1

Evidence That Antibodies to dsDNA Cross React With the A and D SnRNP Proteins.

Fifty-four patients' sera containing anti-nDNA were from SLE patients who satisfied American College of Rheumatology revised criteria for the classification of SLE. 113 sera were obtained from patients without anti-nDNA and were from several groups. Twenty patients without precipitins all satisfied ARA criteria for SLE. Forty-nine sera were from patients with either anti-Ro/SSA precipitins or with both anti-Ro/SSA and anti-La/SSB and having either SLE, subacute cutaneous lupus erythematosus or Sjögren's syndrome. Thirty-four patients with anti-$U_1$RNP precipitins had either SLE, scleroderma, polymyositis or, in a few instances, an overlap of two of these diseases. Multiple samples were obtained on most patients and were immunologically characterized.

Anti-nDNA was measured by the crithidia assay, Aarden, et al., *Ann. NY Acad. Sci.* 254:505–515 (1975). Precipitating antibodies to Ro/SSA, La/SSB, $U_1RNP$, and Sm were assayed by gel diffusion using bovine spleen or calf thymus extracts, using the methods of Clark, et al., *J. Immunol.* 102:117–120 (1969); Mattioli and Reichlin, *Arthritis Rheu.* 17:421–429 (1974). Inhibition of Western blot reactivity against the A and D proteins is accomplished by preincubating appropriate dilutions of the human sera for 1 h at room temperature with calf thymus DNA, Sigma Chemical Co., St. Louis, Mo., at a final concentration of 50 µg/ml. DNA concentrations are assessed by optical density at 260 nm using an extinction value of 1.0 at 50 µg/ml. Solid phase assays for anti-$U_1$RNP and anti-Sm, as well as affinity purification of $U_1$RNP and Sm, were performed as described by Reichlin "Measurement of antibodies to Sm and uRNP by ELISA: clinical and serological correlations. In Mixed Connective Tissue Disease and Anti-Nuclear Antibodies. Kasukawa and Sharp, ed. (Excerpta medica, Elsevier Science Pub., Amsterdam (1987) pp. 85–96).

Antibodies to nDNA were purified with DNA cellulose which contains double-stranded DNA, Sigma Chemical Co., St. Louis, Mo. The DNA cellulose was equilibrated with a buffer containing 0.02M Tris 0.145M NaCl pH 7.2. Sera were dialyzed against this buffer and then applied to the column. Effluents were collected until the OD at 280 nm fell below 0.01 and then reconstituted to the original serum volume by concentration by the Centriprep™ method, Amicon Corp., Danvers, Mass. Specific antibody was eluted with 3M $MgCl_2$, dialyzed against the Tris-NaCl buffer, and assayed for anti-nDNA by the Crithidia assay. These eluates were also concentrated to the volume of the serum from which they were prepared. Gamma globulin concentration was measured using an OD value of 1.5/ mg protein at 280 nm.

SLE sera containing anti-dsDNA (40 of 54 or 74.1%) bound two proteins of 34 and 16 kD in Molt-4 extract, the size of the SnRNP A and D protein. It was hypothesized that these were the A and D SnRNP proteins because reactivity with these bands was depleted from anti-dsDNA sera by DNA cellulose columns. Only 9 of 113 SLE sera without dsDNA bound these two proteins in Western blot. Antibodies to dsDNA correlated closely with anti-A and D in 7 of 8 patients followed sequentially, r=0.7865. Of nine human polyclonal anti-dsDNA isolated from DNA cellulose columns, seven reacted equally with A and D, and two reacted predominantly with D. Two of three murine monoclonal anti-dsDNA antibodies isolated from NZB/NZW $F_1$ hybrid mice bound A and D equally in Western blot with a titer greater than 1/40,000.

EXAMPLE 2

There is an IgM Counterpart of the IgG Anti-dsDNA with Cross Reactivity with the SnRNP A and D Proteins.

As described below, it has now been shown that IgM anti-A and D proteins, but not IgG anti-A and D proteins, are a common finding in sera with anti-Ro/SSA, or both anti-Ro/SSA and anti-La/SSB precipitins, as well as lupus sera without any precipitins, as shown in Table 1. These three groups total 183 sera and exclude sera with anti-Sm and/or anti-$U_1$RNP precipitins.

TABLE 1

Prevalence of Sera with only IgM anti-A and D Protein Antibodies in Western blot.

| Disease and/or Precipitin | Number | IgM Positive Only |
|---|---|---|
| Anti-Ro/SSA (SLE, SCLE, SS) | 110 | 29 |
| Anti-Ro and anti-La (SLE, SCLE, SS) | 32 | 7 |
| SLE (anti-Sm) | 12 | 0 |
| SLE (anti-Sm/nRNP) | 18 | 0 |
| SLE or overlap (anti-nRNP) | 34 | 0 |
| SLE (no precipitins) | 41 | 12 |

Note that 47 of 183 sera in the three groups mentioned above, or 25.7%, have IgM anti-A and D without IgG anti-A and D. Interestingly, none of 64 sera with anti-Sm and/or anti-$U_1$RNP precipitins had only IgM anti-A and D, although more than 90% of the anti-Sm sera had IgG anti-A and D, as did 20% of the anti-$U_1$RNP sera. Thus, IgM anti-A and D is a common feature of SLE sera which lack anti-Sm or anti-$U_1$RNP precipitins. ($X^2$=19.6, p less than 0.000001, odds ratio greater than 1000). This statistic refers to the comparative prevalence of IgM anti-A and D in sera without anti-Sm or anti-$U_1$RNP precipitins to those with anti-Sm or anti-$U_1$RNP precipitins (n=64).

To assess the cross-reactivity of this IgM anti-A and D with anti-dsDNA, these sera were assayed in ELISA on dsDNA coated plates. The results are shown in Table 2.

TABLE 2

Relationship of Western Blot for IgM Anti-A and D with IgM Anti-dsDNA.

| Disease and/or Precipitin | Number | Anti-A and D, dsDNA | A and D | dsDNA |
|---|---|---|---|---|
| Anti-Ro/SSA (SLE, SCLE, SS) | 110 | 20 | 9 | 0 |
| Anti-Ro and La (SLE,SCLE,SS) | 32 | 3 | 4 | 0 |
| SLE with No Precipitins | 41 | 7 | 5 | 1 |

As shown, 30 of the 48 sera with IgM anti-A and D also had IgM anti-dsDNA. Only one serum had IgM anti-dsDNA without IgM anti-A and D. This strengthens the relationship of IgM anti-A and D to IgM anti-dsDNA similar to what is described for the IgG anti-dsDNA and anti-A and D reactions. In addition, the IgM A and D reactions in Western blot can be blocked by addition of between 5 and 50 µg/ml of dsDNA, but not RNA, similarly to the IgG anti-A and D. Thus, there is a strong association of the IgM anti-dsDNA and anti-A and D reactivities. $X^2$=100, odds ratio =201, p less than $10^{30}$.

The patients with IgM anti-dsDNA and IgM anti-A and D have milder disease and a very low prevalence of nephritis. The relationship of IgM and anti-dsDNA to milder disease has been long recognized. The significance of this finding is the demonstration that the relationship of the anti-dsDNA to the A and D cross reactivity extends the previous observations made with the IgG class to the IgM class.

EXAMPLE 3

Human IgG Monoclonal Anti-dsDNA Cross React with SnRNP A and D Proteins.

The studies with mouse monoclonal anti-dsDNA antibodies and human polyclonal anti-dsDNA were confirmed with studies using human IgG monoclonal antibodies to dsDNA described by Winkler, et al., *Clin. Exp. Immunol.,* 85:379–385 (1991). At concentrations of 1 µg/ml these monoclonal antibodies all bind the SnRNP A and D proteins of Molt-4 extract in Western blot. This result eliminates any question about the specificity of the antibodies in a polyclonal autoimmune serum which are reacting with the A and D proteins in Western blot. In addition, there are numerous steps in the development of assays (i.e., the specificity of peptide sequences which serve as the epitope or antigenic determinant responsible for the cross reactivity of the SnRNP A and D proteins) which are optimally validated by reactivity with monoclonal antibodies. Monoclonal antibodies showing these dual specificities (anti-dsDNA on the one hand and anti-A and D on the other) will invariably be superior in fine specificity studies to polyclonal anti-dsDNA isolated from patients in that they represent a single specificity and the results will not be obscured by "dilution" with anti-dsDNA antibodies which lack this dual specificity.

EXAMPLE 4

Validation of the Specificity of the Cross Reaction of Anti-dsDNA with the SnRNP A and D Proteins.

All of the original observations used a whole cell lysate of Molt-4 cells, a malignant T cell line, as the antigen source for the SnRNP A and D proteins. The reactions with the cell lysate were validated with affinity purified $U_1RNP$ as a source of A and D. However, it is still possible that even this affinity purified material has other proteins of identical size with A and D which co-purify. Accordingly, two forms of recombinant D protein were obtained from Dr. Sally Hoch of the Agouron Institute in La Jolla, Calif., and a cDNA clone encoding the A protein was obtained from Dr. Jack Keene of Duke University and used to express recombinant A protein.

Several experiments with Sm D were performed which confirm in detail the original findings. Five of five SLE sera with anti-dsDNA that bind D in crude extracts strongly bind recombinant D (100%). Normal human sera do not bind recombinant D. The two mouse monoclonal anti-dsDNA, two human monoclonal anti-dsDNA, and one affinity purified anti-dsDNA antibody were tested and they all strongly bind recombinant D (100%). These same sera, eluates, and monoclonals with anti-dsDNA specificity will also be tested with recombinant A.

These results provide powerful evidence for the molecular nature of the two bands in Molt-4 of molecular weight 34 and 16 kD which support the identity of the proteins being the SnRNP A and D proteins.

EXAMPLE 5

Pathogenic Effects of Murine and Human Anti-dsDNA on Cells in Culture.

Results have been obtained that show that both murine monoclonal and human polyclonal anti-dsDNA antibodies can bind to, penetrate, and injure cells in culture. Moreover, there is a correlation of the ability of the anti-dsDNA antibodies to bind A and D SnRNP proteins with the ability to mediate cell injury.

Studies were performed with three murine monoclonal antibodies: BWds1, BSds3 and 5GD5, whose reactivity with A and D was determined in Western blot. The first two monoclonals bind A and D while 5GD5 does not. The first two are pathogenic in mice while the third one is not. The pathogenic monoclonals have also been shown to bind and injure pig kidney epithelial cells in culture. One of these (BWd53) requires complement for its cytotoxic effect while the other (BWds1) does not fix complement but penetrates the cell and eventually over a period of days injures the cells. The non-pathogenic monoclonal antibody 5GD5 which does not bind the A and D proteins does not bind the cells in culture.

Similar experiments were also performed with affinity purified polyclonal human anti-dsDNA and similar results obtained. Cross reaction with the A and D SnRNP proteins is associated with the ability to bind, penetrate and injure cells in culture.

EXAMPLE 6

Antibodies to La/SSB and $U_1RNP$ are Anti-Idiotypes to Anti-dsDNA.

Experiments were designed to remove anti-La/SSB and anti-$U_1$RNP from lupus sera which, before this removal, neither contained IgG anti-dsDNA antibody nor bound the SnRNP A and D proteins. Affinity purified La/SSB or $U_1$RNP were used to absorb appropriate sera containing antibodies to these RNA proteins. Sera were tested in Western blot and ELISAs for anti-dsDNA before and after absorption. With six anti-La/SSB sera and five anti-$U_1$RNP sera, the absorbed sera exhibited IgG antibody activity against the SnRNP A and D bands in Western blot against Molt-4 extract. In addition, antibody activity against dsDNA appeared after the absorption. Data from the $U_1$RNP absorbed sera are shown in Table 3.

TABLE 3

Antibody Activity to dsDNA After Absorption of Anti-$U_1$RNP Sera by Affinity Purified $U_1$RNP-Assay in ELISA for dsDNA.

| Human Serum No. | $O.D._{410}$ After Absorption | $O.D._{410}$ Before Absorption |
|---|---|---|
| 195 | .495 | .170 |
| 817 | .695 | .437 |
| 1118 | .674 | .217 |
| 1137 | .740 | .294 |
| 1546 | .831 | .025 |

Mean ± S.D. .686 ± .125  .299 ± .152

These results are interpreted to mean that anti-La/SSB and anti-$U_1$RNP are anti-idiotypes (or anti-antibodies) to anti-dsDNA and removal of the anti-idiotype (anti-La/SSB or anti-$U_1$RNP) by antigen unmasks the idiotype; in this case anti-dsDNA.

EXAMPLE 7

Definition of Reactive Epitope Which Mediates Antigenic Relationship Between SnRNP A and D Proteins and Development of Immunoassay.

In order to develop the appropriate immunoassays and possible immunotherapies based on tolerance induction, it is necessary to determine the structure of the dominant epitopes in the SnRNP A and D proteins which determine the cross reaction between anti-dsDNA and the denatured SnRNP A and D proteins.

Since these reactivities are seen thus far only in Western blot, the epitopes are assumed to be short linear amino acid sequences; i.e., they are so-called sequential determinants. The A and D sequence can be screened by the Pepscan method (Geysen, H. M., Meloen, R. H. and Barteling, S. J., *Proc. Nat. Acad. Sci. USA*, 81:3998–4002, 1984) which is adequate for identification of sequence dependent epitopes which are bound by isolated polyclonal human anti-dsDNA, monoclonal murine or human anti-dsDNA. Alternatively, or in addition, one can look for epitope(s) shared between the A and D proteins by visually scanning the A and D sequences. There are three octapeptide sequences which share at least a tetrapeptide sequence if one permits conservative substitutions such as Ileu for Leu or Lys for Arg as shown in Table 4.

TABLE 4

Paired A and D Octapeptides to a Recognized Epitope Which are Antigenic for Lupus Sera.

| | | | | | | | | |
|---|---|---|---|---|---|---|---|---|
| 1 | | | | | | | | |
| D | | 5 | | | | | | 12 |
| | Arg | Phe | Leu | Met | Lys | Leu | Ser | His |
| | | | (Seq. ID No. 1) | | | | | |
| A | | 275 | | | | | | 282 |
| | Met | Lys | Ileu | Ser | Phe | Ala | Lys | Lys |
| | | | (Seq. ID No. 2) | | | | | |
| 2 | | | | | | | | |
| D | | 41 | | | | | | 48 |
| | Lys | Ala | Val | Lys | Met | Thr | Leu | Lys |
| | | | (Seq. ID No. 3) | | | | | |
| A | | 16 | | | | | | 23 |
| | Asn | Leu | Asn | Glu | Lys | Ileu | Lys | Lys |
| | | | (Seq. ID No. 4) | | | | | |
| 3 | | | | | | | | |
| D | | | | | | | | |
| | Lys | Ser | Lys | Lys | Arg | Glu | Ala | Val |
| | | | (Seq. ID No. 5) | | | | | |
| A | | 105 | | | | | | 112 |
| | Asp | Arg | Lys | Arg | Glu | Lys | Arg | Lys |
| | | | (Seq. ID No. 6) | | | | | |

These paired octapeptides are reasonable candidates for sharing an epitope(s) and the following strategy is proposed in parallel with the overlapping peptide strategy. These six octapeptides can be synthesized using known methodology. These are excellent reagents for coating ELISA plates and can also be conjugated to solid supports by activating the carboxyl group with carbodiimide and attaching the activated peptide to sepharose for affinity chromatography, using reagent manufacturer's instructions. Such MAP peptides have also been used successfully to immunize animals.

For example, peptides can be synthesized in bulk (milligram quantities) on a branching poly-lysine (Maps™, Applied Biosystems, CA) backbone. Maps™ is a pyramid of fifteen lysines upon which eight peptides are added to form a multiple antigenic structure. These reagents allow the screening of large numbers of lupus and normal control sera.

These octapeptides are then used to coat Immunlon™ microtiter plates (Costar, Cambridge, Mass.) and screened for binding to murine or human monoclonal anti-dsDNA antibodies or human polyclonal anti-dsDNA antibodies in ELISAs. If they are bound by one or both members of the pair, the ability of one peptide to inhibit the reactivity of the other with the affinity purified anti-dsDNA will then be tested.

These two approaches: (1) screening the entire sequence by the Pepscan™ method, and (2) testing the pairs of known epitopes with sequence similarity in A and D can be used to identify the cross reactive epitope(s) on the A and D proteins which cross react with either murine or human anti-dsDNA. Competition experiments done by methods well known to those skilled in the art should establish the relative affinity of dsDNA, the A and D proteins, and the reactive peptides.

EXAMPLE 8

Development of Peptide- or Protein-based Immunoassay for Clinical Use in Diagnosis and Prognosis.

Once the reactive peptide epitope is delineated, this can be used as a coating antigenic reagent (e.g., as a MAP™ peptide) in a solid phase based ELISA. The assay is first validated against the Western blot data. It is expected that the ELISA will detect all of the anti-dsDNA antibodies that bind the SnRNP A and D proteins in Western blot since ELISA is 10 to 100 times more sensitive than Western blot. An alternative strategy is to use Western blotting with crude extract as a screening assay.

If the two bands are seen, their specificity would be assured by inhibiting their development by 50 μg/ml DNA as described in Example 1.

This method is slow, cumbersome, and non-quantitative. A second strategy involves development of an ELISA based assay in which coats are plated with recombinant A and recombinant D; the reactions should be nearly identical. This method is simple, quantitative, easy to automate, and quality control would be straightforward.

By far, the best strategy is to identify the peptide epitope (s) and then construct quantitative ELISA's which will be specific, quantitative, simple, easy to automate, and the antigen is synthesized by established chemical methods, and thus in infinite supply.

For clinical purposes a test would still have to be done for anti-dsDNA since not all anti-dsDNA cross reacts with A and D, yet all anti-dsDNA is specific for SLE. A hypothetical Table 5 shows how the tests would work and what diagnostic information and prognostic information would flow from the performance of the tests.

For the purposes of the table, the anti-dsDNA test used would be the crithidia assay, but there are other tests which could also be used. An ELISA for anti-dsDNA is easy to design as a kit in which anti-peptide epitope and anti-dsDNA are measured in the same assay.

TABLE 5

Use of Detection of Antibody to dsDNA and Cross Reactive Epitope on SnRNP.

| Diagnosis | Disease Activity | Prognosis | Anti-dsDNA Crithidia | Anti-A & D Peptide |
|---|---|---|---|---|
| Normal 0 | 0 | | 0 | 0 |
| SLE + | 4+ | Severe Disease | | + |
| SLE + | tr to 1+ | Mild | | 0 |
| SLE 0 | tr to 1+ | Mild | | + |

These tests would not detect all SLE patients, since at most 90% of active untreated SLE patients have anti-dsDNA which includes IgG anti-dsDNA. However, they measure a very important facet of anti-dsDNA; i.e., which ones are likely to cause or be associated with active severe disease and which ones indicate a more serious prognosis with the clinical correlates of anti-dsDNA, especially nephritis.

EXAMPLE 9

Development of Peptide- or Protein-based Immunoassay for Clinical Use in Diagnosis and Prognosis.

The assays and methods of treatment described herein are based on the interpretation of the foregoing data showing that absorption of anti-La/SSB and anti-$U_1$RNP are in an idiotypic network relationship. Thus, anti-La/SSB is an anti-idiotype of anti-A and D (or vice versa) and anti-$U_1$RNP is an anti-idiotype to anti-A and D or vice versa.

The studies reported above used anti-$U_1$RNP sera not reactive with A or D proteins in Western blot before absorption. The experiments were done by absorption in the fluid phase with La/SSB or $U_1$RNP added to small amounts of serum, generally between 10 and 15 μg La/SSB or $U_1$RNP added to 2.5 μl serum or 4.5 mg pure antigen/ml serum which is a large antigen excess. After 2 hours incubation the material is spun down and the supernatant is brought to 250 μl with PBS. Thus the serum reaches a final dilution of 1:100, at which point it is used to develop Western blots and is compared to unabsorbed sera.

These experiments are based on serological tests without separation and purification of the reactants; i.e., the anti-La/SSB or the anti-$U_1$RNP on the one hand and the unmasked anti-A and D antibodies on the other hand, which also apparently have anti-dsDNA activity in many instances.

The most rigorous way to do the absorption so that free antigen cannot in any way complicate the interpretation of the experiments or introduce artifacts is to covalently bind La/SSB or $U_1$RNP to sepharose and then absorb the sera with La/SSB or $U_1$RNP coated beads. This is done until it leads to unmasking of anti-A and D reactivity in Western blot.

Once anti-La/SSB antibodies are isolated they can be then studied for their reactivity with isolated unmasked anti-A and D or affinity purified anti-dsDNA in the following way. The isolated unmasked antibody with anti-A and D activity or isolated affinity purified anti-dsDNA can be pepsin digested and used to coat Immunlon™ plates. Reactivity of whole anti-La/SSB with plates coated with pepsin digested anti-A and D ($Fab_2$) can be studied by detection with a Y chain specific antibody conjugated with alkaline phosphatase. There will only be color development after addition of substrate if the whole IgG anti-La/SSB binds to the plate. Standard variations of this technology can be used to screen large numbers of relevant related or unrelated antibodies.

Anti-La/SSB or anti-$U_1$RNP antibodies affinity isolated in this way can be rigorously tested for their inhibitory reactivity with anti-dsDNA reacting with dsDNA coated plates or in inhibiting anti-dsDNA reacting in the Crithidia assay without interference by excess free antigen.

The rationale for isolating the anti-La/SSB and anti-$U_1$RNP antibodies as well as the unmasked antibodies is to permit the rigorous quantitative study of the interaction between and among such antibodies. This also avoids potential artifacts being introduced by not separating all of the reactants and relying completely on serological methods. It also permits the study of the interaction of these reactants between different patients in order to identify a broadly cross reactive anti-La/SSB or anti-$U_1$RNP that can be used to down regulate anti-dsDNA in unrelated patients.

Modifications and variations of the present invention will be obvious to those skilled in the art and are intended to come within the scope of the appended claims.

---

We claim:

1. A method for determining the presence of IgG antibodies cross-reactive with antibodies to double stranded DNA and denatured anti-A and D SnRNP proteins in a lupus patient, wherein the antibodies are associated with the development of severe disease and nephritis, comprising:

determining if the patient produces anti-dsDNA antibodies, and reacting the anti-dsDNA antibodies with denatured A and D SnRNP proteins to determine if the patient has anti-dsDNA antibodies immunoreactive with denatured A and D SnRNP proteins, wherein the presence of antibodies reactive with dsDNA and denatured A and D proteins is associated with the development of severe disease and nephritis.

2. A method for detecting the presence of anti-idiotypic antibodies in the blood, plasma or serum of a lupus patient wherein the anti-idiotypic antibodies bind to anti-dsDNA antibodies comprising:

a) adsorbing the blood, plasma or serum with La/SSB or URNP$_1$; and b) measuring for the presence of anti-dsDNA antibodies in the absorbed blood, plasma or serum and in nonadsorbed blood, plasma or serum from the same patient wherein the presence of anti-dsDNA antibodies in a greater amount in the adsorbed blood, plasma or serum relative to nonadsorbed blood, plasma or serum indicates the presence of the anti-idiotypic dsDNA antibodies.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: Internal ( x i ) SEQUENCE DESCRIPTION: SEQ ID NO:1:

Arg Phe Leu Met Lys Leu Ser His
    1                      5

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear (i i) MOLECULE TYPE: peptide (i i i) HYPOTHETICAL: NO (i v) ANTI-SENSE: NO (v) FRAGMENT TYPE: Internal (x i) SEQUENCE DESCRIPTION: SEQ ID NO:2:

Met Lys Ile Ser Phe Ala Lys Lys
1               5

(2) INFORMATION FOR SEQ ID NO:3:

(i) SEQUENCE CHARACTERISTICS:
        (A) LENGTH: 8 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: Internal (x i) SEQUENCE DESCRIPTION: SEQ ID NO:3:

Lys Ala Val Lys Met Thr Leu Lys
1               5

(2) INFORMATION FOR SEQ ID NO:4:

(i) SEQUENCE CHARACTERISTICS:
        (A) LENGTH: 8 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: Internal (x i) SEQUENCE DESCRIPTION: SEQ ID NO:4:

Asn Leu Asn Glu Lys Ile Lys Lys
1               5

(2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: Internal (x i) SEQUENCE DESCRIPTION: SEQ ID NO:5:

Lys Ser Lys Lys Arg Glu Ala Val
1               5

( 2 ) INFORMATION FOR SEQ ID NO:6:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:6:

```
Asp  Arg  Lys  Arg  Glu  Lys  Arg  Lys
 1                    5
```